(12) United States Patent
Omote et al.

(10) Patent No.: US 10,145,808 B2
(45) Date of Patent: Dec. 4, 2018

(54) BEAM GENERATION UNIT AND X-RAY SMALL-ANGLE SCATTERING APPARATUS

(71) Applicant: RIGAKU CORPORATION, Akishima-shi, Tokyo (JP)

(72) Inventors: Kazuhiko Omote, Akishima (JP); Kazuki Ito, Akishima (JP)

(73) Assignee: RIGAKU CORPORATION, Tokyo (JP)

( * ) Notice: Subject to any disclaimer, the term of this patent is extended or adjusted under 35 U.S.C. 154(b) by 198 days.

(21) Appl. No.: 15/114,209

(22) PCT Filed: Feb. 2, 2015

(86) PCT No.: PCT/JP2015/052879
§ 371 (c)(1),
(2) Date: Jul. 26, 2016

(87) PCT Pub. No.: WO2015/146287
PCT Pub. Date: Oct. 1, 2015

(65) Prior Publication Data
US 2017/0010226 A1    Jan. 12, 2017

(30) Foreign Application Priority Data
Mar. 27, 2014 (JP) .................. 2014-066608

(51) Int. Cl.
*G01N 23/201* (2018.01)
*G21K 1/10* (2006.01)
*G21K 1/06* (2006.01)

(52) U.S. Cl.
CPC ............ *G01N 23/201* (2013.01); *G21K 1/06* (2013.01); *G21K 1/10* (2013.01);
(Continued)

(58) Field of Classification Search
CPC ........... G01N 23/201; G01N 2223/054; G01N 2223/056; G01N 2223/315; G21K 1/06; G21K 1/10
See application file for complete search history.

(56) References Cited

U.S. PATENT DOCUMENTS 7,646,849 B2    1/2010    Iwasaki et al.
8,249,220 B2    8/2012    Verman et al.
(Continued)

FOREIGN PATENT DOCUMENTS

JP    6-130002 A    5/1994
JP    9-049811 A    2/1997
(Continued)

OTHER PUBLICATIONS

Fewster, "Multicrystal X-ray Diffraction of Heteroepitaxial Structures," Applied Surface Science, vol. 50, No. 1-4, Jun. 2, 1991, pp. 9-18, XP024449684.
(Continued)

*Primary Examiner* — Mark R Gaworecki
(74) *Attorney, Agent, or Firm* — Birch, Stewart, Kolasch & Birch, LLP (57) ABSTRACT

A micro beam generation unit capable of simultaneously capturing anisotropic images in a high signal-to-background ratio with a compact configuration and an X-ray small-angle scattering apparatus are provided. A micro beam generation unit 110 generates X-rays having a micro spot size, with which a sample is irradiated, in order to detect diffracted X-rays by a one-dimensional detector or a two-dimensional detector. The micro beam generation unit 110 includes a slit 115 that is provided on an X-ray optical path and reshapes X-rays into parallel beams, and two channel-cut monochromator crystals 117 and 118 that are arranged in arrangement of (+, −, −, +) and remove parasitic scattering of parallel beams reshaped by the slit. Accordingly, it is possible to
(Continued)

simultaneously obtain anisotropic images in a high signal-to-background ratio with a compact configuration.

16 Claims, 10 Drawing Sheets

(52) U.S. Cl.
CPC . *G01N 2223/054* (2013.01); *G01N 2223/056* (2013.01); *G01N 2223/315* (2013.01)

(56) References Cited

U.S. PATENT DOCUMENTS

| | | |
|---|---|---|
| 9,153,351 B2 | 10/2015 | Tache et al. |
| 2008/0013685 A1 | 1/2008 | Iwasaki et al. |
| 2011/0085644 A1 | 4/2011 | Verman et al. |
| 2013/0064354 A1 | 3/2013 | Tache et al. |

FOREIGN PATENT DOCUMENTS

| | | |
|---|---|---|
| JP | 2001-066398 A | 3/2001 |
| JP | 2002-286658 A | 10/2002 |
| JP | 2008-014861 A | 10/2002 |
| JP | 3468623 B2 * | 11/2003 |
| JP | 2008-014862 A | 1/2008 |
| JP | 2013-508683 A | 3/2013 |

OTHER PUBLICATIONS

MacDowell et al., "Submicron X-ray Diffraction," Nuclear Instruments and Methods in Physics Research. Section A, vol. 467-468, Jul. 21, 2001, pp. 936-943, XP004298861.

Servidori, "X-ray Monochromator Combining High Resolution with High Intensity," Journal of Applied Crystallography, vol. 35, No. 1, Jan. 31, 2002, pp. 41-48, XP009500702.

Sutter et al., "Performance of Multi-crystal Bragg X-ray Spectrometers under the Influence of Angular Misalignments," Nuclear Instruments and Methods in Physics Research. Section A, vol. 589, No. 1, Apr. 21, 2008 (Available online Mar. 10, 2008), pp. 118-131, XP022695402.

Vandenberg et al., "High-resolution X-ray Diffraction Studies of InGaAs(P)/InP Superlattices Grown by Gas-source Molecular-beam Epitaxy," Journal of Applied Physics, vol. 62, No. 4, Aug. 15, 1987, pp. 1278-1283, XP001416798.

"Bonse-Hart camera(USAXS)", [online], Jul. 2, 2013, ESRF(European Synchrotron Radiation Facility), 5 pages, Retrieved from the Internet, URL:http://www.esrf.eu/UsersAndScience/Experiments/SoftMatter/ID02/ BeamlineLayout/EH1.

Matsuoka et al., "Ultra-small-angle x-ray-scattering study: Preliminary experiments in colloidal suspensions", Proc. Natl. Acad. Sci. USA, vol. 88, Aug. 1991, pp. 6618-6619.

* cited by examiner

BEAM GENERATION UNIT AND X-RAY SMALL-ANGLE SCATTERING APPARATUS

TECHNICAL FIELD

The present invention relates to a beam generation unit that generates X-rays with which a sample is irradiated in order to detect scattered X-rays or diffracted X-rays, and an X-ray small-angle scattering apparatus.

BACKGROUND ART

Conventionally, an apparatus configuration for forming parallel X-ray beams by arranging three slits is known as an apparatus for measuring X-ray small-angle scattering because of a need of irradiation of X-rays whose scattering angle is small in X-ray small-angle scattering measurement (Patent Document 1, Non-Patent Document 1). A slit is used to form thin beams, but when X-ray beams hit the end of the slit, parasitic scattering occurs and a tail is left in the scattering angle direction outside the generated beams. In the apparatus with three slits, parasitic scattering is removed by the second and third slits provided with a distance in between. However, in such an apparatus, it is necessary to provide a distance between the slits, and therefore, an apparatus with large dimensions is necessary.

Figure 7:
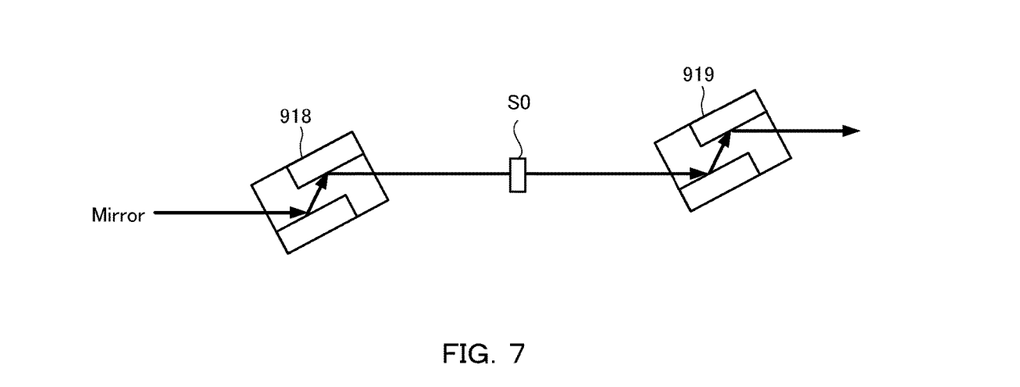
FIG. 7 is a plan view showing an optical system using the conventional Bonse-Hart method.

On the other hand, the apparatus or the like is known that uses the Bonse-Hart method of detecting diffracted rays by a zero-dimensional detector while scanning a channel-cut monochromator crystal arranged on the beam-receiving side (Patent Documents 2 and 3, Non-Patent Document 2). FIG. 7 is a plan view showing an optical system that uses the conventional Bonse-Hart method. In the Bonse-Hart method, as shown in FIG. 7, a sample S0 is irradiated with X-rays generated by making X-rays reflected from the mirror enter a collimator 918 and the X-rays scattered by the sample are detected by reaching of the X-rays to an analyzer 919. In the apparatus configured by such an optical system, the scattered beams in the scattering angle direction are removed and thus measurement with a high resolution is made possible. However, it is not possible to simultaneously obtain anisotropic patterns by a one-dimensional detector or a two-dimensional detector.

In contrast to this, the apparatus described in Patent Document 1 cuts parasitic scattering of a pinhole collimator by the channel-cut monochromator crystal and performs detection with the two-dimensional detector. However, with such an apparatus, the nature of the X-ray to tend to diverge is left and the beams spread because the tail is not removed sufficiently. The reason is that the channel-cut monochromator crystals can be arranged only in arrangement of (+, -, +, -) and therefore, it is not possible to remove the tail caused by the spatial divergence.

PRIOR ART DOCUMENTS

Patent Documents

Patent Document 1: US Patent Laid-Open No. 2013/0064354
Patent Document 2: Japanese Patent Laid-Open No. 2008-014861
Patent Document 3: Japanese Patent Laid-Open No. 2008-014862
Patent Document 4: Japanese Patent Laid-Open No. H06-130002

Non-Patent Documents

Non-Patent Document 1: Hideki Matsuoka, Koji Kakigami, Norio Ise, Yuji Kobayashi, Yoshio Machitani, Tetsuo Kikuchi, Toshiyuki Kato, Ultra-small-angle x-ray-scattering study: Preliminary experiments in colloidal suspensions, Proc. Natl. Acad. Sci. USA, August 1991, vol. 88, pp. 6618-6619
Non-Patent Document 2: Bonse-Hart camera (USAXS), [online], 2013. 7. 2, ESRF (European Synchrotron Radiation Facility), URL: http://www.esrf.eu/UsersAndScience/Experiments/SoftMatter/ID02/BeamlineLayout/EH1

DISCLOSURE OF THE INVENTION

Problem to be Solved by the Invention

As described above, it is difficult to simultaneously obtain anisotropic images and to sufficiently remove the divergence of beams in the images with a compact apparatus configuration by any of the conventional methods.

The present invention has been made in view of such circumstances and an object of the present invention is to provide a beam generation unit capable of simultaneously obtaining anisotropic images in a high signal-to-background ratio with a compact configuration, and an X-ray small-angle scattering apparatus.

Means for Solving Problem (1) In order to achieve the above-described object, the beam generation unit of the present invention is a beam generation unit that generates X-rays with which a sample is irradiated in order to detect scattered X-rays or diffracted X-rays, the beam generation unit including: a slit that is provided on an X-ray optical path and reshapes an X-ray beam shape; and two channel-cut monochromator crystals that are arranged in arrangement of (+, -, -, +), remove parasitic scattering of parallel beams reshaped by the slit, and generate parallel and micro X-ray beams.

As described above, the beam generation unit of the present invention enables an analysis with a high resolution by removing the spatial beam tail as well as removing scattering due to the slit because the channel-cut monochromator crystals are arranged in the arrangement of (+, -, -, +) in the rear stage of the slit. Further, as compared to the three-slit configuration, it is possible to reduce the distance from the X-ray source to the sample and to reduce the apparatus size. Furthermore, by detecting scattered X-rays or diffracted X-rays with a one-dimensional detector or a two-dimensional detector, it is possible to simultaneously measure anisotropic patterns without moving the detector.

(2) Further, the beam generation unit of the present invention further includes a first mirror that is arranged in the front stage of the slit, reflects X-rays within an optical path plane that is formed by the two channel-cut monochromator crystals, and prevents divergence of X-rays in a direction vertical to the optical path plane. Due to this, it is possible to prevent the divergence of beams with which the sample is irradiated and to secure a sufficient intensity.

(3) Further, in the beam generation unit of the present invention, the first mirror is a focusing mirror that forms a focal point on the detector. Due to this, it is possible to increase the intensity while making micro the beam spot with which the sample is irradiated.

(4) Further, in the beam generation unit of the present invention, the two channel-cut monochromator crystals each have a pair of symmetric cut faces. Due to this, it is made easier to arrange and adjust the channel-cut monochromator crystals.

(5) Further, in the beam generation unit of the present invention, one of the two channel-cut monochromator crystals has a pair of asymmetric cut faces. Due to this, it is possible to generate X-ray beams having even higher degree of parallelization and a high intensity.

(6) Further, the beam generation unit of the present invention further includes a second mirror that is arranged in the front stage of the slit, performs reflection within a plane vertical to the optical path plane that is formed by the two channel-cut monochromator crystals, and reshapes divergent beams into parallel beams within the optical path plane. Due to this, it is possible to generate X-ray beams with a high luminance and to increase the intensity of the X-ray beams.

(7) Further, the X-ray small-angle scattering apparatus of the present invention includes a goniometer that mounts the above-described beam generation unit on a rotary arm. Due to this, it is possible to measure small-angle scattering in a free direction within the drive range of the rotary arm of the goniometer. For example, it is also possible to store a liquid and irradiate the liquid with X-rays from below.

(8) Further, the X-ray small-angle scattering apparatus of the present invention further includes a two-dimensional detector that detects scattered X-rays or diffracted X-rays generated by irradiation of a sample with X-rays generated by the beam generation unit. Due to this, it is possible to detect the X-rays scattered at a small angle by the sample with a high angular resolution.

Effect of the Invention

According to the present invention, the channel-cut monochromator crystals are arranged in the arrangement of (+, −, −, +) in the rear stage of the slit, and therefore, it is possible to simultaneously obtain anisotropic images in a high signal-to-background ratio with a compact configuration.

BRIEF DESCRIPTION OF THE DRAWINGS

FIGS. 4 (a) to 4 (d) are plan views each showing a beam generation unit.

MODES FOR CARRYING OUT THE INVENTION

Next, an embodiment of the present invention will be explained with reference to the drawings. In order to make it easier to understand explanation, the same reference numeral is attached to the same component in each drawing, and duplicate explanation will be omitted.

[First Embodiment]
(X-Ray Small-Angle Scattering Apparatus)

X-ray small-angle scattering is a method of analyzing the structure of a substance by measuring scattered X-rays whose scattering angle is small (normally, 10° or less) among scattered X-rays when the substance is irradiated with X-rays. If the wavelength of the X-ray is taken to be $\lambda$, the scattering angle is taken to be $2\theta$, from Bragg's law $\lambda = 2d \sin \theta$, measuring scattered X-rays whose scattering angle is smaller corresponds to measuring a larger structure in the real space. Common sizes measured by the small-angle scattering are 1 to 100 nm, and therefore, it is possible to analyze a structure at the level of several nanometers, such as internal structures of a fine particle, a liquid crystal, and an alloy, by the small-angle scattering.

Figure 1:
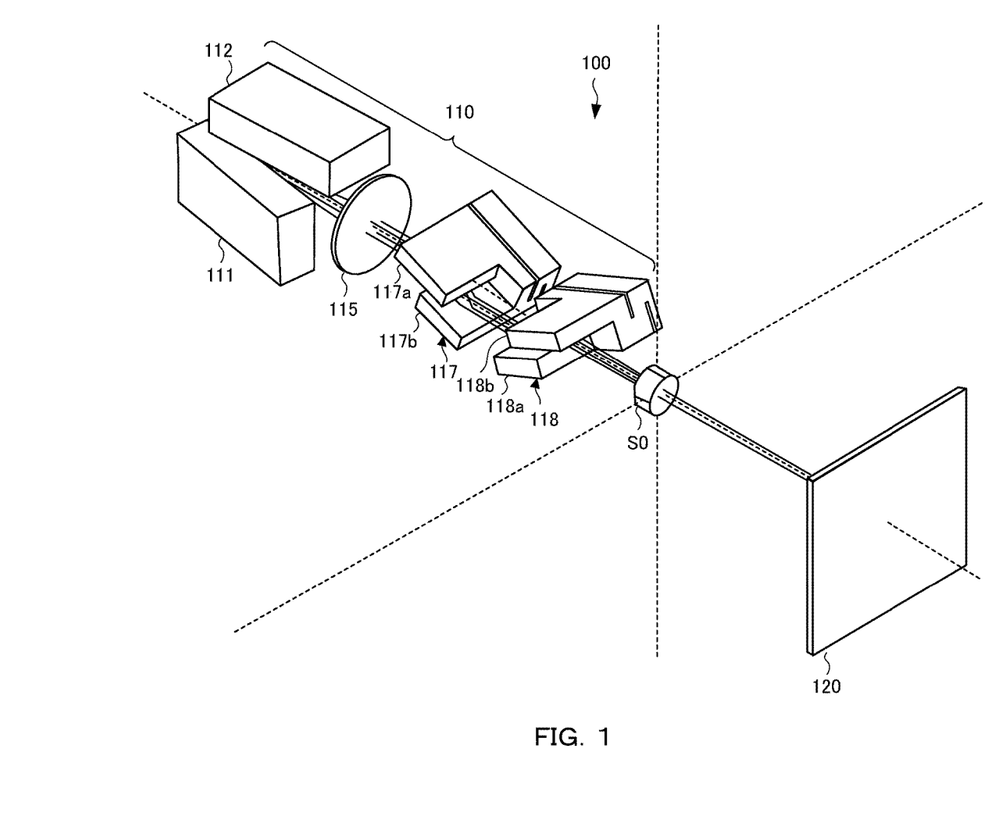
FIG. 1 is a perspective view showing an X-ray small-angle scattering apparatus of the present invention.
Figure 2:
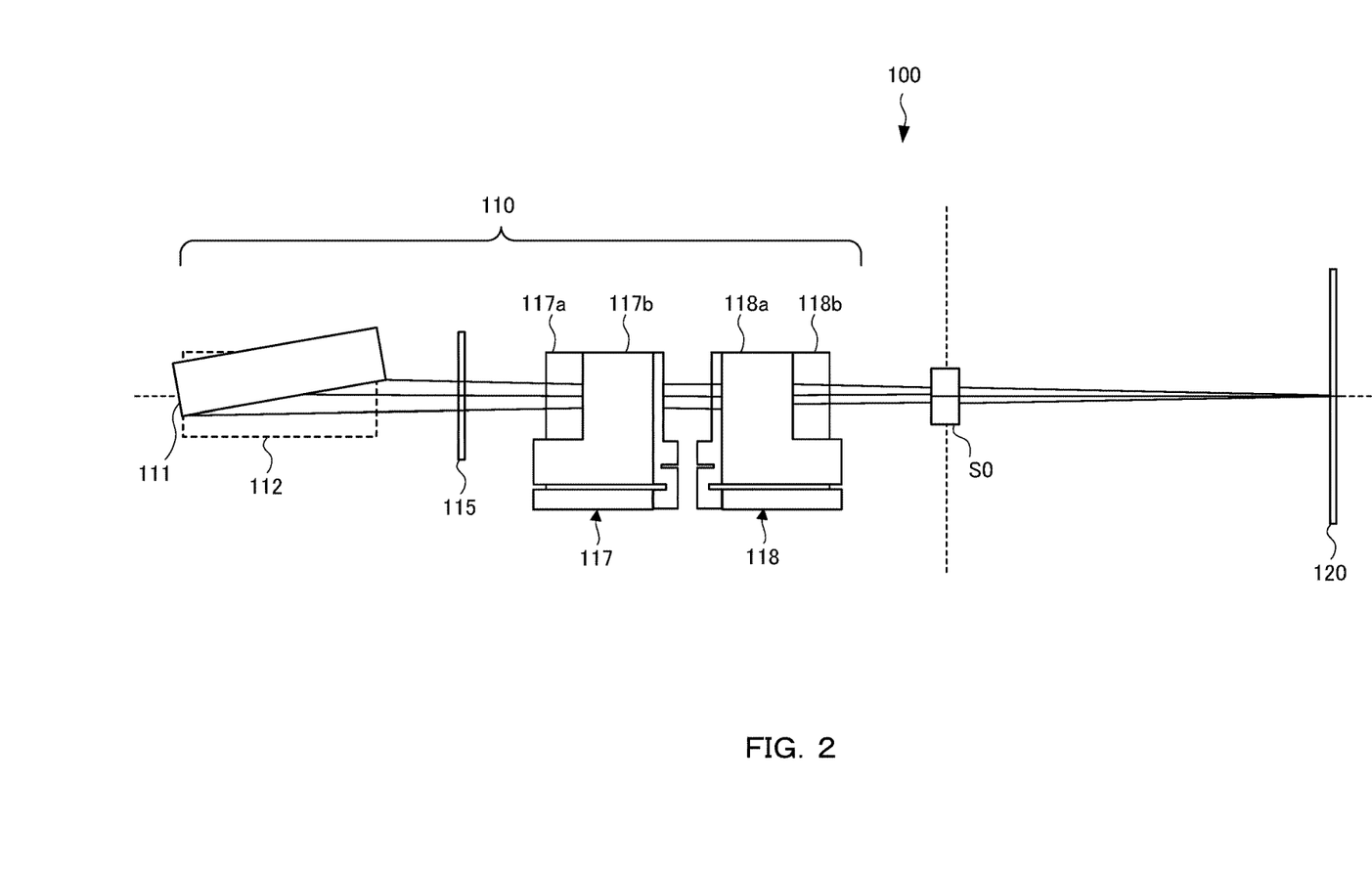
FIG. 2 is a side view showing the X-ray small-angle scattering apparatus of the present invention.
Figure 3:
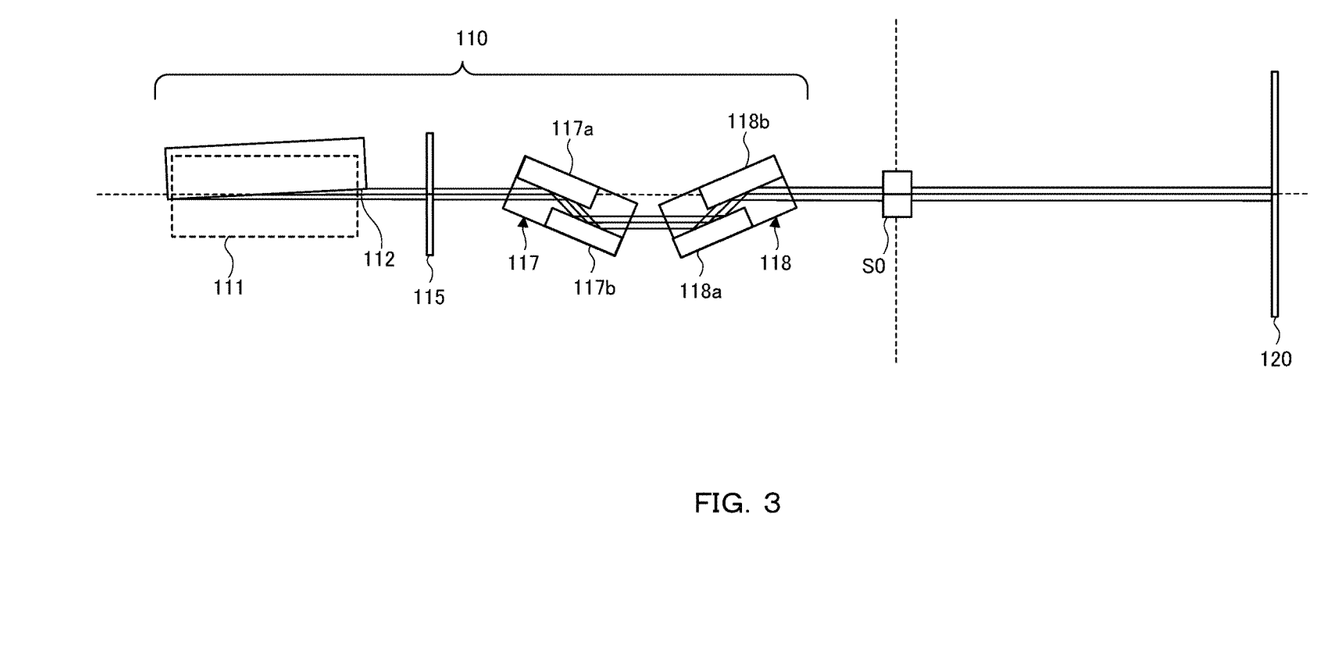
FIG. 3 is a plan view showing the X-ray small-angle scattering apparatus of the present invention.
Figure 4A:
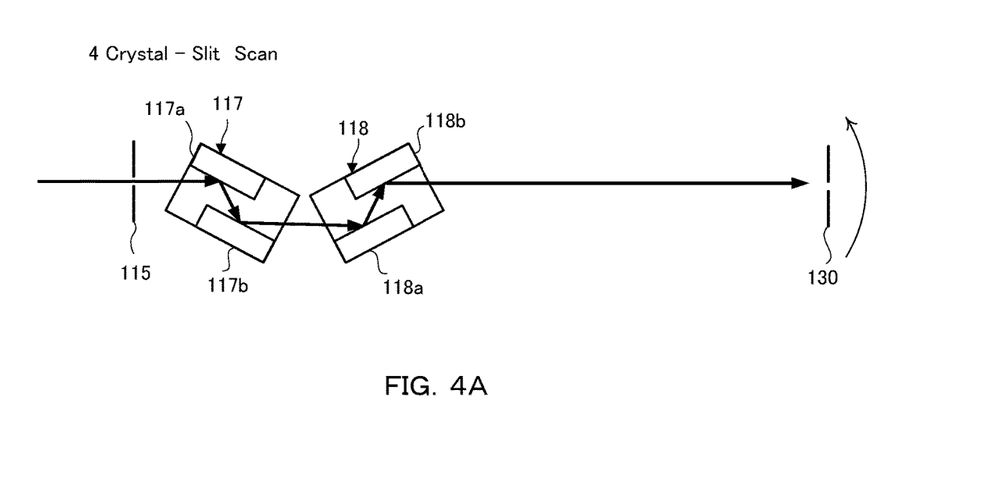
Figure 4B:
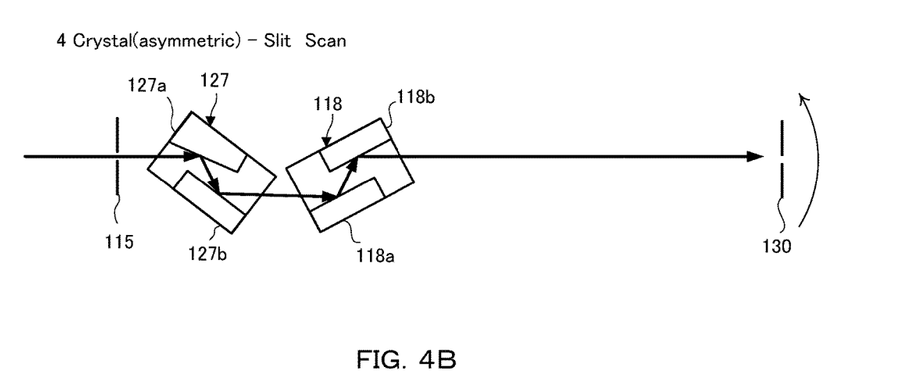
Figure 4C:
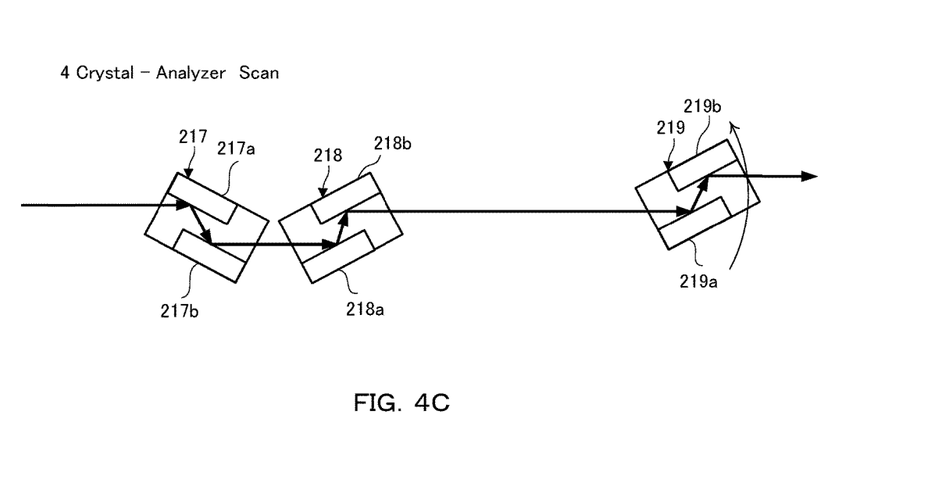
Figure 4D:
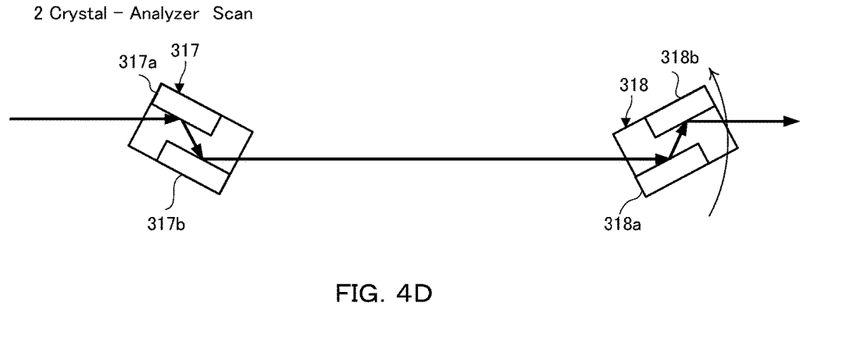

FIG. 1 to FIG. 3 are a perspective view, a side view, and a plan view, respectively, showing an outline of an X-ray small-angle scattering apparatus 100. As shown in FIG. 1 to FIG. 3, the X-ray small-angle scattering apparatus 100 includes an X-ray source, a beam generation unit 110, a goniometer, and a detector 120.

It is preferable to use a micro point X-ray source of 0.1 mm or less (micro-focus X-ray source) as the X-ray source. Due to this, it is possible to form a focal point having a micro spot size and a high intensity. Here, in the outline configuration shown in FIG. 1 to FIG. 3, the X-ray source is omitted.

(Beam Generation Unit)

The beam generation unit 110 generates X-rays that are parallel and have a micro spot size, with which a sample S0 is irradiated, and detects diffracted X-rays with a one-dimensional detector or a two-dimensional detector. Note that, as the detector 120, a one-dimensional detector or a two-dimensional detector is used, and therefore, it is possible to simultaneously obtain anisotropic diffraction patterns.

The beam generation unit 110 includes a first mirror 111, a second mirror 112, a slit 115, and two channel-cut monochromator crystals 117 and 118. In each of the two channel-cut monochromator crystals 117 and 118, a pair of crystals having diffraction planes that reflect X-rays are arranged.

It is preferable for the beam generation unit 110 to be used to detect X-rays scattered at a small angle by irradiating the sample S0 with generated beams at a fine angle. Due to this, it is possible to generate X-ray micro beams suitable for use application of the small-angle scattering. As a result of this, for example, it is possible to measure small-angle scattering with respect to a small particle of 100 nm or less. Note that, the use application of the beam generation unit 110 is not necessarily limited to the small-angle scattering, but the beam generation unit 110 is particularly effective for the small-angle scattering.

(First Mirror)

The first mirror 111 is arranged in the front stage of the slit 115 and reflects X-rays within an X-ray optical path plane that is formed by the two channel-cut monochromator crystals 117 and 118, and prevents the divergence of X-rays in the direction vertical to the above-described X-ray optical path plane. As a result of this, it is possible to secure a sufficient intensity by preventing the divergence of beams with which the sample S0 is irradiated within the optical path plane formed by the two channel-cut monochromator crystals 117 and 118. By arranging the first mirror 111 in order to secure intensity, it is made possible to sufficiently detect scattering even in the case where the scattering is caused by a sample of a polycrystalline substance or an amorphous substance other than a single crystal.

It is preferable for the first mirror 111 to be a focusing mirror that curves with a predetermined curvature and forms a focal point on the detector 120. Due to this, it is possible to increase intensity while keeping micro the beam spot with which the sample S0 is irradiated.

For example, a case is considered where the first mirror 111 is an elliptic mirror, the distance from the X-ray source to the sample S0 is 700 mm, and the camera length is set to 400 to 500 mm. At this time, in the case where beam is focused within 0.3 mm by the first mirror 111 having a range of approximately 0.8°, arctangent when the base is 700 mm and the height is 0.3 mm is about 0.4 mrad.

In this case, the ratio in intensity between presence and absence of the first mirror 111 is 0.8°=14 mrad/0.4 mrad=35. In this manner, it is possible to increase intensity by focusing X-rays thus spread by the first mirror 111. Here, it is supposed that the reflectance of the mirror is one, but actually, it is slightly smaller than one. Further, the first mirror 111 may be a parabolic mirror, provided that there is no divergence.

(Second Mirror)

The second mirror 112 is a mirror that curves with a predetermined curvature, is arranged in the front stage of the slit 115, reflects X-rays generated in the X-ray source within the plane vertical to the optical path plane formed by the two channel-cut monochromator crystals 117 and 118, and reshapes divergent beams into parallel beams within the above-described optical path plane. As a result of this, it is possible to generate X-ray beams with a high luminance and to increase the intensity of the X-ray beams.

The second mirror 112 makes constant the focal length of the incident X-ray. It is possible for the second mirror 112 to reshape beams having a focal point size in accordance with the use application. For example, it is possible to further increase intensity by changing a focal point size of 70 μm into that of 100 μm to 200 μm. It is possible for the second mirror 112 to increase the beam width to about 1 mm at the maximum. It is possible to increase intensity by increasing the beam width as above. As the second mirror 112, a parabolic mirror may be used and it is also possible to generate beams having a desired focal point size with the slit 115 and further to adjust the size with the second mirror 112.

Note that, in the case of the optical system that uses the conventional Bonse-Hart method, whether beams are parallel in the direction vertical to the optical path plane is not known, and therefore, it is possible to accurately measure the degree of parallelization only in the direction parallel to the optical path plane. It is possible for the beam generation unit 110 to generate parallel beams also in the direction vertical to the optical path plane by arranging the second mirror 112. Further, the angular resolution within the optical path plane is increased by reducing the spot size of the X-ray beam. By providing a focusing element within the optical path plane and by reducing the beam size in the direction vertical to the optical path plane, beams whose beam divergence in the direction parallel to the plane is also natural and which are parallel with a small width of the crystal are emitted. After all, angle information with a high accuracy within the plane vertical to the optical path plane is obtained two-dimensionally, not only in the one-dimensional direction.

As shown in FIG. 1, it is possible to use the first mirror 111 and the second mirror 112 as an integrated mirror in which the two mirrors are vertically bonded to each other, but it may also be possible to provide them separately. Depending on which kind of mirror is used as these mirrors, it is possible to give priority to intensity by increasing the focal point size or to increase resolution by reducing the focal point size.

Note that, in the case where the first mirror 111 is installed in a position close to the X-ray source and the second mirror 112 is installed in a position close to the sample S0, the X-rays generated in the X-ray source are reflected from the first mirror 111 and the second mirror 112 in this order and then the X-rays are caused to enter the two channel-cut monochromator crystals 117 and 118 as a result. However, it is not necessary to limit the arrangement and an arrangement in which the positions of these components are exchanged may be accepted.

Further, as the first mirror 111 or the second mirror 112, it is possible to use any of a total reflection mirror, a multilayer film mirror, and a crystal plate. The total reflection mirror is formed by curving a glass plate itself or a reflection plate or the like formed by forming a film of Ni (nickel), Au (gold), Pt (platinum), etc., on the surface of a glass plate.

The multilayer film mirror is formed by alternately stacking layers having different electron densities a plurality of times on a substrate having a smooth surface. By repeating a multilayer stack structure periodically with a plurality of layers, it is possible to efficiently diffract specific X-rays, for example, CuK α-rays. As the material of the substrate, a glass plate, a silicon wafer or the like is used. The crystal plate may be formed by using a single crystal plate of α-$SiO_2$ (quartz), Si (silicon), Ge (germanium) or the like.

(Slit)

The slit 115 is provided on the X-ray optical path and reshapes the X-ray beam shape. The shape of the hole of the slit 115 is not limited, and the shape may be that of a line or a quadrangle, but preferably, the shape is that of a circular pinhole in order to prevent scattering from the edge of the slit 115.

(Channel-Cut Monochromator Crystal)

The two channel-cut monochromator crystals 117 and 118 are arranged in the arrangement of (+, −, −, +) in the rear stage of the slit 115 and remove scattering of parallel beams reshaped by the slit 115. Due to such an arrangement, the analysis with a high resolution is made possible by removing the spatial beam tail as well as eliminating scattering caused by the slit 115. As a result of this, it is also possible to use the beam generation unit 110 for detection of so-called small-angle scattering. Further, as compared to the configuration of a apparatus that uses three slits, it is possible to reduce the distance from the X-ray source to the sample S0.

The channel-cut monochromator crystal is parallel walls on both sides that are used for reflection when a groove is cut in the single crystal block. The crystal block consists of a one-piece crystal in its entirety, and therefore, all the X-rays Bragg-reflected from one of the crystal walls are Bragg-reflected from the other crystal wall. The channel-cut monochromator crystal is formed by machining a perfect crystal of germanium or silicon to cut a groove. By causing X-rays to reflect from a pair of X-ray reflecting surfaces formed on both sides of the groove, monochromatic beams with a high accuracy are obtained.

The first channel-cut monochromator crystal 117 is arranged on the X-ray incidence side of the second channel-cut monochromator crystal 118 and has a first crystal 117*a* and a second crystal 117*b*, and in each of the crystals 117*a* and 117*b*, cut faces in opposition to each other are formed.

The first channel-cut monochromator crystal 117 is arranged so that X-rays diffracted by the first channel-cut monochromator crystal 117 enter the second channel-cut monochromator crystal 118. Further, the first channel-cut monochromator crystal 117 has a shape and arrangement capable of diffracting X-rays by the crystal plane having the same indices as those of the crystal plane by which the second channel-cut monochromator crystal 118 diffracts X-rays, and of causing the X-rays to enter the second channel-cut monochromator crystal 118.

The second channel-cut monochromator crystal 118 has a third crystal 118a and a fourth crystal 118b and on each crystal wall thereof, cut faces in opposition to each other are formed.

The arrangement of (+) or (−) in the channel-cut monochromator crystal refers to the arrangement of the crystal that diffracts X-rays in the bending direction that is determined based on the bending direction of the first diffraction being taken to be (+). Consequently, the arrangement of the crystal that diffracts X-rays in the same bending direction as the bending direction of the first diffraction is (+) and the arrangement of the crystal that diffracts X-rays in the bending direction opposite to the bending direction of the first diffraction is (−).

The first channel-cut monochromator crystal 117 is provided so as to be capable of diffracting X-rays in the arrangement of (+, −) with respect to incident X-rays. The second channel-cut monochromator crystal 118 is provided in the position where X-rays diffracted by the first channel-cut monochromator crystal 117 can enter, so as to be capable of diffracting X-rays in the arrangement of (−, +) with respect to incident X-rays. In this manner, it is possible to reshape the X-ray beam sectional shape into a square or a circle.

In the beam generation unit 110, the scattering of the slit 115 can be removed by the channel-cut monochromator crystals 117 and 118 and it is possible to generate beams that produce no tail, but if an attempt is made to implement a configuration that prevents scattering to the same extent as this with three pinholes, approximately 1.5 m is necessary as the distance from the X-ray source to the sample S0. The beam generation unit 110 as described above can be configured with a reduced distance of 10 cm to 15 cm and it is possible to place the sample S0 immediately behind the beam generation unit 110.

It is preferable for the four crystals 117a, 117b, 118a, and 118b to be formed by twos as each of the channel-cut monochromator crystals 117 and 118, but a combination of those formed separately may be accepted.

With such a configuration, the channel-cut monochromator crystals 117 and 118 diffract X-rays in the rear stage of the slit 115 and remove the X-rays of parasitic scattering whose direction has been changed by the slit 115. Further, by arranging the two channel-cut monochromator crystals 117 and 118, not only the divergence $\Delta\theta$ (divergence) in the direction of the divergence angle of the X-ray beams but also the dispersion $\Delta\lambda$ ($\Delta E$) of the wavelength (energy) is removed at the same time. With the conventional configuration, even if $\Delta\theta$ is limited, the width of $\Delta E$ increases, and therefore, the tail is formed due to passing-through to a certain extent, but with the configuration of the beam generation unit 110, this can be removed.

As described above, with the beam generation unit 110, the wavelength dispersion can also be removed, but the intensity of X-rays is apt to be reduced accordingly. However, this reduction in intensity can be compensated for by the first mirror 111.

As the material of the crystal that can be used for these channel-cut monochromator crystals 117 and 118, mention is made of germanium or silicon, but the material is not limited to those. Further, as the crystal plane that is used, for example, mention is made of Ge (220).

(Goniometer)

The goniometer mounts the beam generation unit 110 on a first rotary arm. The first rotary arm is made rotatable with respect to the sample S0. Due to this, it is possible to measure small-angle scattering in the drive range of the first rotary arm of the goniometer. For example, although a liquid is difficult to seal, it is possible to irradiate a liquid with X-rays after storing the liquid in a vessel.

As described above, the beam generation unit 110 is configured so as to be compact, and therefore, it is possible to perform measurement by mounting the beam generation unit 110 on the rotary arm of the goniometer and freely changing the direction, and it is also possible to use beams radiated from below to above and beams radiated from above to below.

Further, the goniometer includes a $\theta$ rotary disc and a second rotary arm. The $\theta$ rotary disc and the second rotary arm have a configuration in which when the $\theta$ rotary disc rotates by an angle $\theta$ around the same rotation axis, the second rotary arm rotates by an angle $2\theta$ in accordance with this in an interlocking manner.

On the $\theta$ rotary disc, a sample table (sample holding unit) is mounted and a sample is held on the sample table. The sample table rotates along with rotation of the $\theta$ rotary disc and a positional relationship with respect to the relative angle between the X-ray incidence plane of the sample held on the sample table and the X-ray source is changed. Due to this, the incidence angle of X-rays with respect to the sample is changed.

On the second rotary arm, the detector 120 is mounted. The detector 120 rotates around the X-ray incidence plane of the sample together with the second rotary arm. Due to this, the positional relationship with respect to the relative angle between the X-ray incidence plane of the sample held on the sample table and the detector 120 is changed and the detector 120 moves up to the position where the diffracted X-rays that are diffracted by the sample are detected. Here, it is possible to arbitrarily set the camera length from the sample S0 to the detector 120 in accordance with an object to be measured. There may be a case where the camera length is approximately 1 m or a case where the camera length is shorter.

Note that, if the X-ray beams with a high degree of parallelization are detected in a position sufficiently distant from the sample, the small-angle scattering measurement is made possible even if the beam size is not micro, but in this case, there arises a necessity to increase the size of the apparatus. For example, in the case of a apparatus that uses the prior art, the size of the apparatus needs to be 10 m to 20 m, but by using the beam generation unit 110, it is possible to use highly parallel and micro beams, and therefore, it is possible to reduce the size of the apparatus to around several meters and to implement the X-ray small-angle scattering apparatus 100 with high compactness.

(Detector)

The detector 120 is arranged in a position where the X-rays diffracted by the sample enter. The detector 120 may be a one-dimensional detector having a position resolution in the straight line direction or a two-dimensional detector having a position resolution within a plane. By using the two-dimensional detector, it is possible to detect X-rays scattered at a small angle by the sample with a high angular resolution. As the one-dimensional detector, mention may be made of a PSPC, a linear CCD sensor, etc. As the two-dimensional detector, mention may be made of a two-dimensional CCD sensor and a photon-counting-type pixel two-dimensional detector.

(Example)

Spectrum measurement of X-ray beams generated by the above-described beam generation unit (example) and by 4-crystal and 2-crystal beam generation units (comparative examples) was performed. FIGS. 4 (a) to 4 (d) are plan views each showing a configuration of beam generation unit. The distance from the X-ray source to the detection position is set to 750 mm in each configuration.

FIG. 4 (a) shows a configuration of a beam generation unit using a slit, in which two channel-cut monochromator crystals are arranged so as to be in the arrangement of (+, −, −, +) in the rear stage of the incident slit 115, 0.1 mm wide, and X-rays are collimated. As the X-ray source, the CuKα-rays are used, as the channel-cut monochromator crystal, the dispersive Ge crystal is used, and Ge (220) is used as the crystal plane (this also applies to the following comparative examples). The collimated X-rays are scanned and detected by a beam-receiving slit 130, 0.1 mm wide.

In place of the configuration shown in FIG. 4 (a), a configuration shown in FIG. 4 (b) may be used. In this case also, two channel-cut monochromator crystals 127 and 118 (four crystals 127a, 127b, 118a and 118b) are arranged so as to be in the arrangement of (+, −, −, +) in the rear stage of the incident slit 115. Then, the channel-cut monochromator crystal 127 has a pair of asymmetric cut faces. Due to this, it is possible to generate X-ray beams having a higher degree of parallelization and a higher intensity. Here, both the two channel-cut monochromator crystals may each have a pair of asymmetric cut faces.

FIG. 4 (c) shows a configuration of the 4-crystal beam generation unit, in which two channel-cut monochromator crystals 217 and 218 (four crystals 217a, 217b, 218a and 218b) are arranged so as to be in the arrangement of (+, −, −, +) and further, one channel-cut monochromator crystal 219 (two crystals 219a and 219b) in the arrangement of (−, +) is used as an analyzer and a scan is performed.

FIG. 4 (d) shows a configuration of the 2-crystal beam generation unit, in which one channel-cut monochromator crystal 317 (two crystals 317a and 317b) is arranged so as to be in the arrangement of (+, −) and further, one channel-cut monochromator crystal 318 (two crystals 318a and 318b) in the arrangement of (−, +) is used as an analyzer and a scan is performed.

Figure 5:
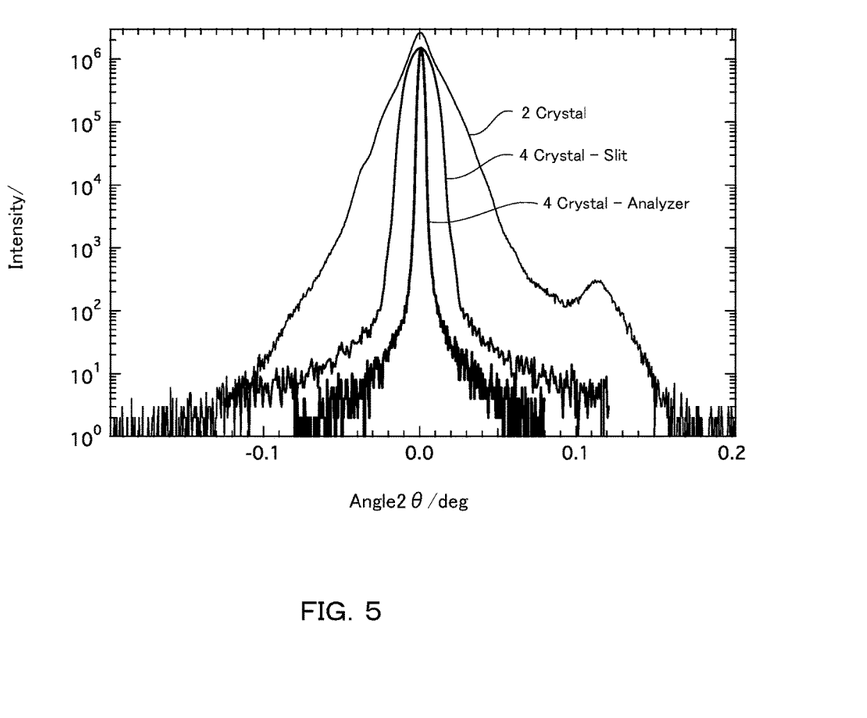
FIG. 5 is a graph representing the intensity for the divergence angle of X-ray beams generated by each beam generation unit.

FIG. 5 is a graph representing the measurement results of the intensity distribution of X-ray beams generated by each beam generation unit. As shown in FIG. 5, with the beam generation unit using a slit and the 4-crystal beam generation unit, it is possible to sufficiently remove the tail. With the 2-crystal beam generation unit, the tail remains. Note that, with the 4-crystal beam generation unit, the tail is removed as with the beam generation unit using a slit, but in this case, it is not possible to perform measurement using a one-dimensional detector or a two-dimensional detector.

Figure 6:
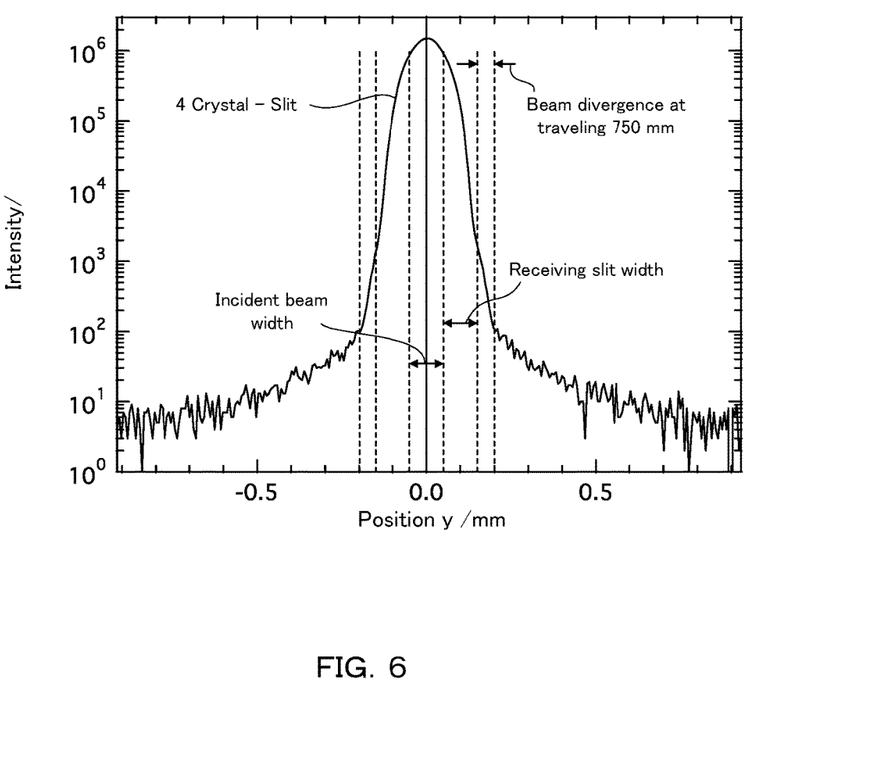
FIG. 6 is a graph representing the intensity for the divergence angle of X-ray beams in an example.

FIG. 6 is a graph representing the measurement results of the intensity distribution of X-ray beams of the example. From the measurement results, it is known that a slight tail is produced, but it is almost zero. Further, depending on a slight difference in detection position, the X-ray intensity is reduced by four or five digits, and therefore, X-ray beams having a rectangular shape and a slight tail are obtained.

DESCRIPTION OF SYMBOLS

100 X-ray small-angle scattering apparatus
110 beam generation unit
111 first mirror
112 second mirror
115 slit
117 first channel-cut monochromator crystal
117a first crystal
117b second crystal
118 second channel-cut monochromator crystal
118a third crystal
18b fourth crystal
20 detector
127 first channel-cut monochromator crystal
130 beam-receiving slit

The invention claimed is:

1. A beam generation unit that generates X-rays with which a sample is irradiated in order to detect scattered X-rays or diffracted X-rays, the beam generation unit comprising:
    a slit that is provided on an X-ray optical path and reshapes an X-ray beam shape;
    two channel-cut monochromator crystals that are arranged in arrangement of (+, −, −, +), remove parasitic scattering of parallel beams reshaped by the slit, and generate parallel and micro X-ray beams; and
    a first mirror that is arranged in a front stage of the slit, reflects X-rays within an optical path plane that is formed by the two channel-cut monochromator crystals, and prevents divergence of X-rays in a direction vertical to the optical path plane.

2. The beam generation unit according to claim 1, wherein the first mirror is a focusing mirror that forms a focal point on a detector.

3. The beam generation unit according to claim 1, wherein the two channel-cut monochromator crystals each have a pair of symmetric cut faces.

4. The beam generation unit according to claim 1, wherein one of the two channel-cut monochromator crystals has a pair of asymmetric cut faces.

5. The beam generation unit according to claim 1, further comprising:
    a second mirror that is arranged in the front stage of the slit, performs reflection within a plane vertical to the optical path plane that is formed by the two channel-cut monochromator crystals, and reshapes divergent beams into parallel beams within the optical path plane.

6. An X-ray small-angle scattering apparatus comprising:
    a goniometer that mounts the beam generation unit according to claim 1 on a rotary arm.

7. The X-ray small-angle scattering apparatus according to claim 6, further comprising:
    a two-dimensional detector that detects scattered X-rays or diffracted X-rays generated by irradiation of a sample with X-rays generated by the beam generation unit.

8. A beam generation unit that generates X-rays with which a sample is irradiated in order to detect scattered X-rays or diffracted X-rays, the beam generation unit comprising:
    a slit that is provided on an X-ray optical path and reshapes an X-ray beam shape; and
    two channel-cut monochromator crystals that are arranged in arrangement of (+, −, −, +), remove parasitic scattering of parallel beams reshaped by the slit, and generate parallel and micro X-ray beams,
    wherein one of the two channel-cut monochromator crystals has a pair of asymmetric cut faces.

9. The beam generation unit according to claim 8, further comprising:

a mirror that is arranged in a front stage of the slit, performs reflection within a plane vertical to an optical path plane that is formed by the two channel-cut monochromator crystals, and reshapes divergent beams into parallel beams within the optical path plane.

10. An X-ray small-angle scattering apparatus, comprising:
a goniometer that mounts the beam generation unit according to claim 8 on a rotary arm.

11. The X-ray small-angle scattering apparatus according to claim 10, further comprising:
a two-dimensional detector that detects scattered X-rays or diffracted X-rays generated by irradiation of a sample with X-rays generated by the bean generation unit.

12. An X-ray small-angle scattering apparatus comprising:
a beam generation unit that generates X-rays with which a sample is irradiated in order to detect scattered X-rays or diffracted X-rays, the beam generation unit including:
a slit that is provided on an X-ray optical path and reshapes an X-ray beam shape; and
two channel-cut monochromator crystals that are arranged in arrangement of (+, −, −, +), remove parasitic scattering of parallel beams reshaped by the slit, and generate parallel and micro X-ray beams; and
a goniometer that mounts the beam generation unit on a rotary arm.

13. The X-ray small-angle scattering apparatus according to claim 12, wherein the two channel-cut monochromator crystals each have a pair of symmetric cut faces.

14. The X-ray small-angle scattering apparatus according to claim 12,
wherein one of the two channel-cut monochromator crystals has a pair of asymmetric cut faces.

15. The X-ray small-angle scattering apparatus according to claim 12, further comprising:
a mirror that is arranged in a front stage of the slit, performs reflection within a plane vertical to an optical path plane that is formed by the two channel-cut monochromator crystals, and reshapes divergent beams into parallel beams within the optical path plane.

16. The X-ray small-angle scattering apparatus according to claim 12, further comprising:
a two-dimensional detector that detects scattered X-rays or diffracted X-rays generated by irradiation of a sample with X-rays generated by the bean generation unit.

* * * * *